(12) United States Patent
Sathe et al.

(10) Patent No.: US 11,266,628 B2
(45) Date of Patent: Mar. 8, 2022

(54) PHARMACEUTICAL COMPOSITIONS OF APREMILAST

(71) Applicant: UNICHEM LABORATORIES LTD, Mumbai (IN)

(72) Inventors: Dhananjay Sathe, Thane (IN); Srikant Pimple, Pune (IN); Pradeep Kumar Gupta, Tikamgarh (IN); Vishal Jadhav, Mumbai (IN)

(73) Assignee: UNICHEM LABORATORIES LTD, Mumbai (IN)

( * ) Notice: Subject to any disclaimer, the term of this patent is extended or adjusted under 35 U.S.C. 154(b) by 0 days.

(21) Appl. No.: 16/754,553

(22) PCT Filed: Oct. 1, 2018

(86) PCT No.: PCT/IB2018/057603
§ 371 (c)(1),
(2) Date: Apr. 8, 2020

(87) PCT Pub. No.: WO2019/073331
PCT Pub. Date: Apr. 18, 2019

(65) Prior Publication Data
US 2020/0261416 A1 Aug. 20, 2020

(30) Foreign Application Priority Data
Oct. 13, 2017 (IN) .............................. 201721036386

(51) Int. Cl.
*A61K 31/4035* (2006.01)
*A61K 9/00* (2006.01)
*A61K 9/20* (2006.01)
*A61K 9/28* (2006.01)

(52) U.S. Cl.
CPC ........ *A61K 31/4035* (2013.01); *A61K 9/0053* (2013.01); *A61K 9/2095* (2013.01); *A61K 9/284* (2013.01); *A61K 9/2866* (2013.01)

(58) Field of Classification Search
CPC .............. A61K 31/4035; A61K 9/2095; A61K 9/2018; A61K 9/2059; A61K 9/0053; A61K 9/2013; A61K 9/284; A61K 9/2866; A61K 9/2853; A61K 9/2813
See application file for complete search history.

(56) References Cited

U.S. PATENT DOCUMENTS

| | | | |
|---|---|---|---|
| 2012/0171288 A1 | 7/2012 | Khullar et al. | |
| 2014/0370092 A1* | 12/2014 | Parikh | A61K 9/2866 424/480 |
| 2015/0344409 A1* | 12/2015 | Shrawat | C07C 213/00 564/360 |

FOREIGN PATENT DOCUMENTS

| | | | |
|---|---|---|---|
| WO | 2013045961 A1 | 4/2013 | |
| WO | WO-2013119607 A2 * | 8/2013 | ......... A61K 31/4035 |
| WO | WO-2016120380 A1 * | 8/2016 | ........... A61K 9/2013 |
| WO | WO-2017004122 A1 * | 1/2017 | .............. A61P 35/04 |

OTHER PUBLICATIONS

International Search Report issued in PCT/IB18/57603, dated May 7, 2019 (2 pages).

\* cited by examiner

*Primary Examiner* — Blessing M Fubara
(74) *Attorney, Agent, or Firm* — Arent Fox LLP

(57) ABSTRACT

The present invention relates to a disintegrant free pharmaceutical composition comprising apremilast or pharmaceutically acceptable salts thereof and one or more pharmaceutically acceptable excipients. Particularly the present invention relates to disintegrant free immediate release dosage form comprising apremilast or pharmaceutically acceptable salts thereof and one or more pharmaceutically acceptable excipients. It further relates to process of preparing such composition and its use in psoriatic arthritis and psoriasis.

9 Claims, 3 Drawing Sheets

FIG. 1: dissolution profile of Otezla® 10 mg tablets (reference) versus apremilast tablets 10 mg (test) as per composition of example 1 in 0.15% SLS in 25mM Sodium phosphate buffer pH-6.8, RPM-60, Vol-900 ml, 37 °C ± 0.5.
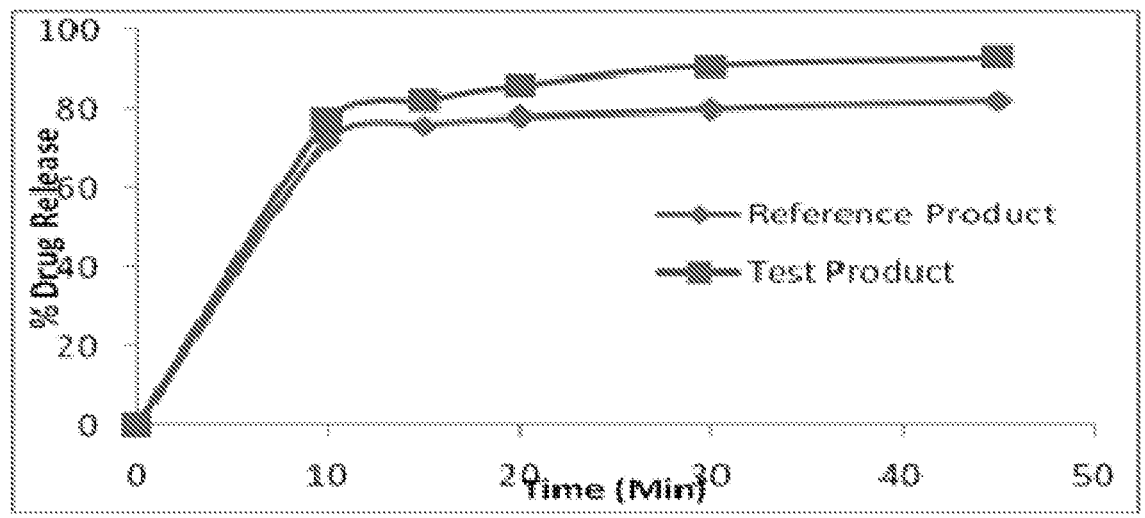

FIG. 2: Dissolution profile of Otezla® 20 mg tablets (reference) versus apremilast tablets 20 mg (test) as per composition of example 1 in 0.15% SLS in 25mM Sodium phosphate buffer pH-6.8, RPM-60, Vol-900 ml, 37 °C ± 0.5.
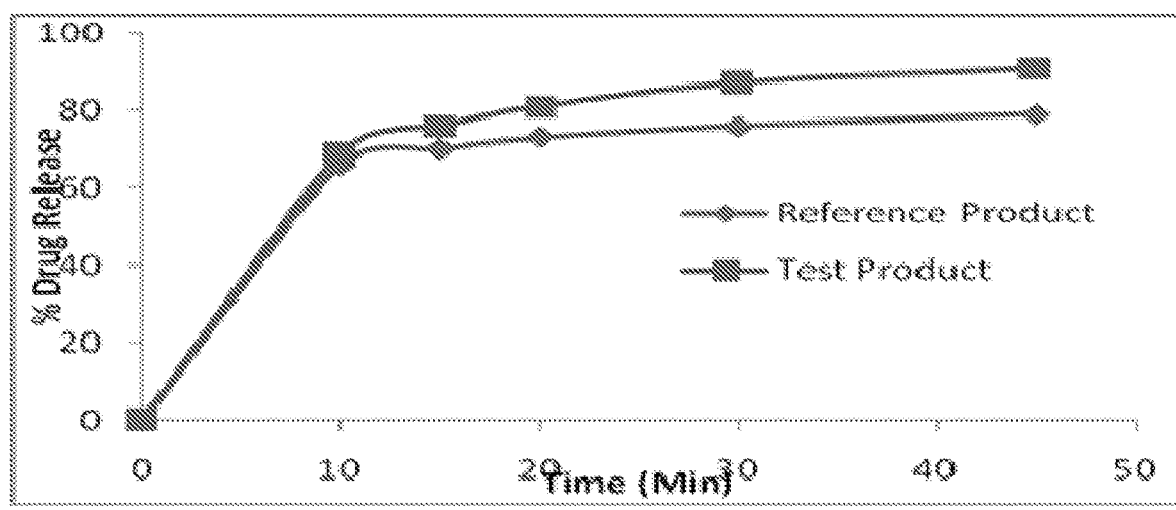

FIG. 3: Dissolution profile of Otezla® 30 mg tablets (reference) versus apremilast tablets 30 mg (test) as per composition of example 1 in 0.15% SLS in 25mM Sodium phosphate buffer pH-6.8, RPM-60, Vol-900 ml, 37 °C ± 0.5.
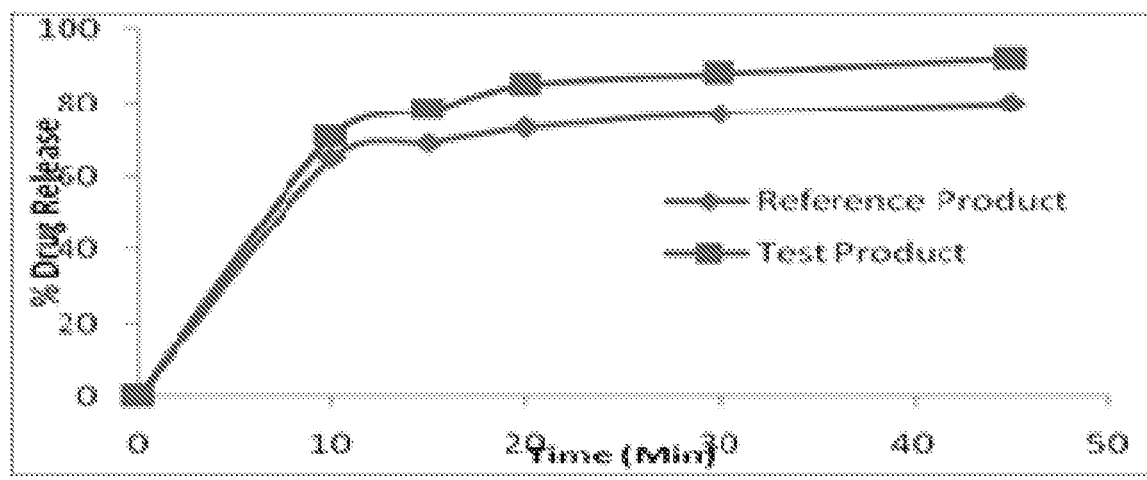

PHARMACEUTICAL COMPOSITIONS OF APREMILAST

FIELD OF THE INVENTION

The present invention relates to a disintegrant freestable pharmaceutical composition comprising apremilast or pharmaceutically acceptable salts thereof and one or more pharmaceutically acceptable excipients.

The present invention also relates to process for preparation of disintegrant free stable pharmaceutical composition comprising apremilast or pharmaceutically acceptable salts thereof and at least one pharmaceutically acceptable excipient.

Further the present invention relates to disintegrant free stable pharmaceutical composition of apremilast or pharmaceutically acceptable salts thereof and one or more pharmaceutically acceptable excipients and its use in psoriatic arthritis and psoriasis.

BACKGROUND OF THE INVENTION

Apremilast is an oral small-molecule inhibitor of phosphodiesterase 4 (PDE4) specific for cyclic adenosine monophosphate (cAMP) and it is indicated for the treatment of psoriatic arthritis and psoriasis.

The IUPAC name for apremilast is, N-[2-[(1S)-1-(3-ethoxy-4-methoxyphenyl)-2-(methylsulfonyl)ethyl]-2,3-dihydro-1,3-dioxo-1H-isoindol-4-yl]acetamide. Its empirical formula is $C_{22}H_{24}N_2O_7S$ and the molecular weight is 460.5. The chemical structure is shown below:

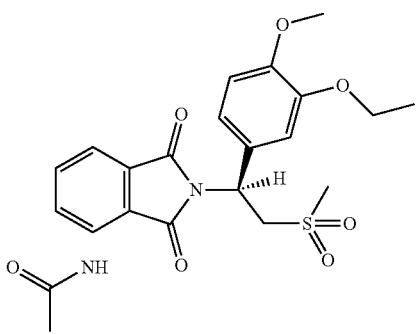

Apremilast is currently available in the market as tablet for oral use under the brand name OTEZLA® in USA market in 10 mg, 20 mg and 30 mg strengths.

U.S. Pat. No. 6,020,358 by Celgene Corporation, discloses apremilast generically.

U.S. Pat. No. 7,893,101 by Celgene Corporation, discloses solid forms of apremilast.

US20150306226 by RatiopharmGmbh, discloses an immediate release composition comprising a melting of apremilast together with pharmaceutically acceptable excipients.

CN104546831 by Hangzhou XinbosiBiolog Medicine Co Ltd, discloses a pharmaceutical composition comprising apremilast and cyclodextrin or a cyclodextrin derivative.

WO2017076987 by Ratiopharm GMBH, discloses a solid solution or solid dispersion of apremilast.

U.S. Pat. No. 9,468,605 by Celgene Corporation, discloses an immediate-release oral dosage form comprising about 10-30% by weight of apremilast, about 40-50% by weight of lactose, about 20-30% by weight of cellulose, about 1-5% by weight of carboxymethyl cellulose, about 1-5% by weight of fumed silica and about 0.1-2% by weight of magnesium stearate and about 1-5% by weight of a coat.

US20130164376 by Celgene Corporation, discloses tablet comprising core composition comprises apremilast at an amount of about 100/by weight of the total core composition; lactose at an amount of about 60% by weight of the total core composition; microcrystalline cellulose at an amount of about 26.25% by weight of the total core composition; croscarmellose at an amount of about 3% by weight of the total core composition; magnesium stearate at an amount of about 0.75% by weight of the total core composition and tablet core is coated with coating composition.

Disintegrating agent is one of the excipients used in tablet formulation, however the use of disintegrant has a few disadvantages such as but not limited to 1) hygroscopic nature of the disintegrant, use of disintegrant in higher percentage must be protected by atmospheric moisture as it may lead to softening of the tablets 2) Requirement of high concentration of disintegrants when used in direct compression as method of tablet manufacture 3) Poor compression properties, and the like.

The objective of the present invention was therefore to overcome the above mentioned disadvantages which leads to processing and manufacturing challenges during tableting operations.

Hence there is unmet need to design more stable, reproducible, cost effective and easy to scale up and bioequivalent composition comprising apremilast.

Accordingly, inventors of the present invention developed disintegrants free stable composition of apremilast and surprisingly found that it is bioequivalent with that of the marketed OTEZLA® composition. The present invention further provides a simple, economical and industrially feasible process for preparing pharmaceutical composition of apremilast.

OBJECT OF THE INVENTION

The main object of present invention is to provide a disintegrant free stable pharmaceutical composition comprising apremilast or pharmaceutically acceptable salts thereof and one or more pharmaceutically acceptable excipient.

Another object of present invention is to provide disintegrant free stable immediate release dosage form comprising apremilast or pharmaceutically acceptable salts thereof and one or more pharmaceutically acceptable excipient.

Yet another object of present invention is to provide process for preparing disintegrant free stable pharmaceutical composition comprising apremilast or pharmaceutically acceptable salts thereof and at least one pharmaceutically acceptable excipient.

Yet another object of the present invention is to provide disintegrant free stable pharmaceutical composition of apremilast or pharmaceutically acceptable salts thereof and one or more pharmaceutically acceptable excipients useful for the treatment of psoriatic arthritis and psoriasis.

SUMMARY OF THE INVENTION

The present invention relates to disintegrant free stable solid oral compositions of apremilast with one or more pharmaceutically acceptable excipients.

In one aspect, the present invention particularly relates to disintegrant free stable immediate release solid tablet composition comprising apremilast or pharmaceutically acceptable salts thereof and one or more pharmaceutically acceptable excipients.

Another aspect, the present invention provides a process for preparation of the disintegrant free stable composition comprising apremilast or pharmaceutically acceptable salts thereof and at least one pharmaceutically acceptable excipient.

In yet another aspect, the present invention provides a process for preparing disintegrant free stable pharmaceutical composition by direct compression comprising the steps of:
i) siftingapremilast or pharmaceutically acceptable salts thereof with one or more pharmaceutically acceptable excipients;
ii) blending the mixture obtained in step (i);
iii) adding lubricant to blended mixture of step (ii) followed by blending to form lubricated blend;
iv) formulating material of step (iii) into a suitable dosage form; and
iv) optionally coating.

In yet another aspect, the disintegrant free pharmaceutical composition of apremilast of the present invention is stable when stored at 40° C.±2° C. & 75%/5% relative humidity for a period of at least six months or to the extent necessary for the use of the composition.

In yet another aspect, the present invention relates to disintegrant free stable pharmaceutical composition of apremilast or pharmaceutically acceptable salts thereof with one or more pharmaceutically acceptable excipients is useful for the treatment of psoriatic arthritis and psoriasis.

BRIEF DESCRIPTION OF THE DRAWING

Features and advantages of the subject matter of the present invention as disclosed herein will become clearer from the detailed description of an embodiment thereof, with reference to the attached drawing, given purely by way of an example, in which:

FIG. 1: Graphical representation of dissolution profile of Otezla® 10 mg tablets herein referred as 'reference' versus apremilast tablets 10 mg herein referred to as 'test' as per composition of example 1 in 0.15% SLS in 25 mM Sodium phosphate buffer pH-6.8, RPM-60, Vol-900 ml, 37° C.±0.5.

FIG. 2: Graphical representation of dissolution profile of Otezla® 20 mg tablets herein referred as 'reference' versus apremilast tablets 20 mg herein referred to as 'test' as per composition of example 1 in 0.15% SLS in 25 mM Sodium phosphate buffer pH-6.8, RPM-60, Vol-900 ml, 37° C.±0.5.

FIG. 3: Graphical representation of dissolution profile of Otezla® 30 mg tablets herein referred as 'reference' versus apremilast tablets 30 mg herein referred to as 'test' as per composition of example 1 in 0.15% SLS in 25 mM Sodium phosphate buffer pH-6.8, RPM-60, Vol-900 ml, 37° C.±0.5.

Various objects, features, aspects and advantages of the inventive subject matter will become more apparent from the following detailed description of preferred embodiments.

DETAILED DESCRIPTION OF THE INVENTION

The invention will now be described in detail in connection with certain preferred and optional embodiments, so that various aspects thereof may be more fully understood and appreciated.

The term "Apremilast" as used herein refers to apremilast free base or in the form of any pharmaceutically acceptable salts or derivatives thereof, including stereoisomer, prodrug, solvate, hydrate, clathrate, metabolite or solid forms, preferably apremilast is N-[2-[(1 S)-1-(3-ethoxy-4-methoxyphenyl)-2-(methylsulfonyl)ethyl]-2,3-dihydro-1,3-dioxo-1H-isoindol-4-yl]acetamide.

Preferably enantiomerically pure form of apremilast is used, more preferably apremilast used in B polymorphic form.

The term "Stereomerically pure" means a composition that one stereoisomer of a compound and is substantially free of other stereoisomers of that compound.

The term "enantiomerically pure" means a stereomerically pure composition of a compound having one chiral center.

The term "composition" or 'pharmaceutical composition" or "dosage form" as used herein interchangeably includes solid dosage forms such as but not limited to granules, pellets, micro-pellets, spheres, cores, coated cores, pills, compressed tablets, mini tablets, layered tablets, beads, particles, capsules and the like, meant for oral administration.

The term "pharmaceutically acceptable" as used herein means that which is useful inpreparing a pharmaceutical composition that is generally safe and non-toxic.

The term "pharmaceutically acceptable salt(s)," as used herein includes, but is not limited to, salts of acidic or basic moieties of apremilast.

The term "excipient" means a pharmacologically inactive compound such as a diluent, a lubricant, a glidant, a binder comprised in a pharmaceutical product. The excipients that are useful in preparing a pharmaceutical composition are generally safe, non-toxic and are acceptable for human use. Reference to an excipient includes both one and more than one such excipients.

The term "tablet" is intended to encompass compressed pharmaceutical dosage forms of all shape and size, whether coated or uncoated.

The term "binder" as used herein means a substance that helps bind the active ingredient and other excipients together in a tablet. Binder ensures that tablets and granules can be formed having desired and required mechanical strength.

The term "Disintegrant free stable pharmaceutical composition" as used herein refers to the pharmaceutical composition of apremilast, which does not contain any disintegrant.

The term "stable and reproducible" as used herein means that the composition is stable when stored at stability conditions as per ICH stability guidelines as well as it is stable during shelf life of the product. The process described herein produces a stable and bioequivalent formulation repeatedly.

The term "stable," as used herein, refers to chemical stability, wherein not more than 1.5% w/w of total related substances are formed on storage at accelerated conditions of stability at 40° C.±2° C. & 75%/5% relative humidity for a period of at least six months or to the extent necessary for use of the composition.

The term "bioequivalent" as used herein means that a formulation that has the same pharmacologic potency and bioavailability as another formulation containing same active agent at the same dose. Two products or formulations containing the same active ingredient are bioequivalent if their rates and extents of absorption i.e., bioavailability are the same.

The term "reference" as used herein means the drug identified by the FDA as the drug product upon which an applicant relies in seeking approval of its Abbreviated New Drug Application (ANDA).

The term "ASTM" as used herein means American Society for Testing and Materials.

The term "RH" as used herein means Relative humidity.

The term "LOD" as used herein means Loss on drying.

The term "BRT" as used herein means Below Reporting Threshold.

The term "BQL" as used herein means Below Quantification Limit.

The term 'similarity factor' or 'f2' as used herein refers to one way of comparing dissolution profiles of two different products. This model-independent mathematical approach compares the dissolution profile of the two products: test and reference or two strengths. Tests are recommended to be performed under the same test conditions. The dissolution time points for both the profiles should be the same. An f2 value of 50 or greater (50-100) ensures sameness or equivalence of two curves, and thus performance of the two products, in-vitro.

The present invention in a preferred embodiment provides a disintegrant free stable pharmaceutical composition comprising apremilast or pharmaceutically acceptable salts thereof and one or more pharmaceutically acceptable excipients.

Inventors of the present invention surprisingly found that a disintegrant free stable pharmaceutical composition comprising apremilastresults into the stable, reproducible and bioequivalent product.

In an embodiment, the present invention can be formulated in the form of solid dosage forms selected from but not limited to granules, pellets, micro-pellets, spheres, cores, coated cores, pills, compressed tablets, mini tablets, layered tablets, beads, particles, capsules and the like.

In a preferred embodiment, the present invention can be formulated into immediate release tablets.

In an embodiment, the oral dosage form comprises one or more of the following excipients such as but not limited to binders, glidants, lubricants, diluents, sweeteners, thickening agents, preservatives, flavoring agents, plasticizers and coloring agent or any combinations thereof.

Diluents or fillers include but are not limited to microcrystalline cellulose, micro fine cellulose, powdered cellulose, lactose, spray dried lactose, lactose monohydrate, dibasic calcium phosphate, tribasic calcium phosphate, starch, pregelatinized starch, calcium carbonate, calcium sulfate, magnesium carbonate, magnesium oxide, dextrates, dextrin, dextrose, kaolin, maltodextrin, mannitol, sucrose, methyl dextrin and sorbitol or any combination thereof.

In a preferred embodiment of the present invention diluent used is lactose monohydrate or any combination thereof.

The composition of the present invention preferably comprises from about 10% to about 90% of one or more diluents by weight based on the total weight of the composition.

Binders include but are not limited to, polyvinylpyrrolidone (povidone, PVP); polyethylene glycol (PEG); cross-linked polyvinylpyrrolidone;polyvinyl Alcohols; polymethacrylates; starch and modified starch, pregelatinized starch, cellulose derivatives includinghydroxymethyl cellulose, hydroxypropylcellulose, carboxy-methylcellulose sodium, ethyl cellulose, hydroxylethylcellose, and hydroxypropylmethylcellulose; sucrose;alginic acid or sodium alginate;carbomer; cottonseed oil; dextrin; dextrose; guar gum; hydrogenated vegetable oil type I; magnesium aluminium silicate; maltodextrin; maltose;polydextrose; polyethylene oxide stearic acid and zein or combination thereof.

One or more binders are preferably used in an amount of from about 1% to about 15% by weight based on the total weight of the composition.

A preferred binder is pregelatinized starch or various commercially available grades thereof.

Lubricants include, but are not limited to magnesium stearate, aluminium stearate, sucrose stearate, stearic acid, talc, fumaric acid, palmitic acid, sodium stearyl fumarate, glyceryl monostearate, carnauba wax, hydrogenated vegetable oils, mineral oil, polyethylene glycols or combination thereof.

Lubricants are preferably used in an amount of from about 0.5% to about 2.0% by weight based on the total weight of the composition.

A preferred lubricant is magnesium stearate or any combination thereof.

In an embodiment of the present invention the pharmaceutically acceptable excipients to be used in accordance with the present invention can be used only intra granularly, only extra granularly or both.

In one of the preferred embodiment, the tablet of the present application optionally be coated with a film coat, which provides an aesthetic appeal. Film coat also provides moisture protection, taste masking and the like.

Film coating material suitable for present application include but not limited to polyvinyl alcohol, hydroxypropyl methylcellulose,carboxymethyl cellulose, polyethylene glycol and like. Preferably the coating is carried out using coating agents for exampleOpadry®. Preferred Opadry® isOpadry II Green, Opadry II White and Opadry II Orange.Opadry II contains polyvinyl alcohol, titanium dioxide, polyethylene glycol, red iron oxide, yellow iron oxide, black iron oxide, FD&C Blue #2/indigo carmine aluminum lake.

In yet another embodiment, the present invention provides a stable a hydrochloride composition when subjected to 40±2° C./75±5% RH accelerated stability condition.

In an embodiment of the invention, the pharmaceutical compositions as described herein may be prepared by processes known to a person having ordinary skill in the art of pharmaceutical technology such as direct compression, wet granulation, dry granulation or melt granulation.

In a preferred embodiment, the disintegrant free stable pharmaceutical composition of the present invention is prepared by direct compression technique.

In an embodiment, the present invention include use of certain packaging material to store active substance or pharmaceutical formulation such as but not limited to containers and lids of HDPE, low-density polyethylene (LDPE) and/or polypropylene and/or glass, and blisters composed of resins of polyvinyl chloride and polyvinyl diene chloride and the like.

In one embodiment the present invention provides a process for preparation of a disintegrant free stable pharmaceutical composition comprising apremilast or pharmaceutically acceptable salts thereof and one or more pharmaceutically acceptable excipients, wherein the process comprises steps of:

i) siftingapremilastor pharmaceutically acceptable salts thereof with one or more pharmaceutically acceptable excipients;
ii) blending the mixture obtained in step (i)
iii) adding lubricant to blended mixture of step (ii) followed by blending to form lubricated blend;

iv) formulating material of step (iii) into a suitable dosage form; and
v) optionally coating the dosage form obtained in step (iii).

In one embodiment the present invention provides a process of preparing a disintegrant free stable pharmaceutical composition comprising apremilast or pharmaceutically acceptable salts thereof according to any one of the preceding claims, comprising the steps of:
i) siftingapremilast, one or more diluent, one or more binders through #30 ASTM sieve;
ii) blending mixture of step (i) in a suitable blender;
iii) prelubricating the blend of step (ii);
iv) sifting lubricant through #60 ASTM sieve and added to step (iii) and blended to form lubricated blend;
v) compressing the lubricated blend of step (iv); and
vi) optionally coating the compressed tablets.

In an embodiment, the disintegrant free pharmaceutical composition of the present invention comprises about 10 mg to about 30 mg of apremilast.

In another embodiment, the disintegrant free stable pharmaceutical composition of apremilast of the present invention is stable when stored at 40° C.±2° C. & 75%±5% relative humidity for a period of at least six months or to the extent necessary for the use of the composition.

In another embodiment, the disintegrant free stable pharmaceutical composition of apremilast of the present invention is useful for the treatment of psoriatic arthritis and psoriasis in a patient in need thereof.

EXAMPLES

The present invention will be described in more detail by way of the following illustrative examples. It should be understood, however, that the present invention or the examples provided herein below are not limited to the specific details, components, conditions described in these examples, and the scope of the present invention is not limited thereto.

Example 1

Composition comprising 10 mg, 20 mg, and 30 mg of Apremilast and preparation of tablet dosage form therefrom:

| Sr. No. | Ingredients | Quantity (mg/Tab) | | | % (w/w) |
|---|---|---|---|---|---|
| | | 10 mg | 20 mg | 30 mg | |
| Dry Mix | | | | | |
| 1 | Apremilast | 10 | 20 | 30 | 10 |
| 2 | Lactose monohydrate | 75 | 150 | 225 | 75 |
| 3 | Pregelatinized Starch | 14 | 28 | 42 | 14 |
| 4 | Magnesium Stearate | 1 | 2 | 3 | 1 |
| Total weight of core tablet (mg) | | 100 | 200 | 300 | — |
| Film Coating | | | | | |
| 5 | OpadryII White | 3 | — | — | 3 |
| 6 | Opadry II Green | — | 6 | — | 3 |
| 7 | Opadry II Orange | — | — | 9 | 3 |
| Total weight of coated tablet (mg) | | 103 | 206 | 309 | — |

Manufacturing Procedure:
1. Dispense all the ingredients as per unit formula;
2. Co-sifting apremilast and lactose monohydrate through sieve #30 ASTM in the ratio 1:2;
3. Mixture of step (2) and pregelatinized starch were co-shifted through sieve #30 ASTM;
4. Mixture of step (3) material and remaining quantity lactose monohydrate were co-sifted through sieve #30 ASTM;
5. Step (4) material loaded in blender and pre-lubrication was performed
6. magnesium stearate passed through sieve #60 ASTM and added to step (5) and lubrication was performed to obtain lubricated blend;
7. The lubricated blend of step (6) was compressed into tablets using suitable punches and dies to obtain core tablet.
8. Film Coating: Prepared of 15% w/w dispersion Opadry dispersion was prepared by slowly adding Opadry II in purified water under vortex and continued stirring for 45 minutes, coating dispersion was sifted through mesh #100 ASTM. Film coating was performed on core tablets of step (7) to obtain coated tablets; and
9. coated tablets of step (8) were packed in HDPE Bottles or and blister pack.

Example 2

Composition comprising 10 mg, 20 mg, and 30 mg of Apremilast and preparation of tablet dosage form therefrom:

| Sr. No. | Ingredients | Quantity (mg/Tab) | | | % (w/w) |
|---|---|---|---|---|---|
| | | 10 mg | 20 mg | 30 mg | |
| Dry Mix | | | | | |
| 1 | Apremilast | 10 | 20 | 30 | 10 |
| 2 | Lactose monohydrate | 87 | 174 | 261 | 87 |
| 3 | Pregelatinized Starch | 2 | 4 | 6 | 2 |
| 4 | Magnesium Stearate | 1 | 2 | 3 | 1 |
| Total weight of core tablet (mg) | | 100 | 200 | 300 | — |
| Film Coating | | | | | |
| 5 | Opadry II White | 3 | — | — | 3 |
| 6 | Opadry II Green | — | 6 | — | 3 |
| 7 | Opadry II Orange | — | — | 9 | 3 |
| Total weight of coated tablet (mg) | | 103 | 206 | 309 | — |

Manufacturing Procedure:
1. Dispense all the ingredients as per unit formula;
2. Co-sifting apremilast and lactose monohydrate through sieve #30 ASTM in the ratio 1:2;
3. Mixture of step (2) and pregelatinized starch were co-shifted through sieve #30 ASTM;
4. Pre-lubricating material of step (3) in a blender;
5. magnesium stearate passed through sieve #60 ASTM and added to step (5) and lubrication was performed to obtain lubricated blend;
6. The lubricated blend of step (6) was compressed into tablets using suitable punches and dies to obtain core tablet.
7. Film Coating: Prepared of 15% w/w dispersion Opadry dispersion was prepared by slowly adding Opadry 11 in purified water under vortex and continued stirring for 45 minutes, coating dispersion was sifted through mesh #100 ASTM. Film coating was performed on core tablets of step (6) to obtain coated tablets; and 8. coated tablets of step (7) were packed in HDPE Bottles or and blister pack.

Comparison of In-Vitro Dissolution Profile:

The tablets of apremilast prepared as per the composition of Example 1 were subjected to dissolution studies.

TABLE 1

Provides comparative dissolution profiles of Otezla ®10 mg herein referred as 'reference' versus apremilasttablets10 mg as per composition of Example 1, herein referred to as 'test'in 0.15% SLS in 25 mM sodium phosphate buffer pH-6.8, RPM-60, Vol-900 ml at 37 ± 0.5° C.

| Time points | Cumulative percent drug release | | | |
|---|---|---|---|---|
| | Reference Product | | Test Product | |
| (minutes) | pH - 6.8 | % RSD | pH - 6.8 | % RSD |
| 10 | 72 | 3.8 | 77 | 2.12 |
| 15 | 76 | 3.97 | 82 | 1.67 |
| 20 | 78 | 2.39 | 86 | 1.80 |
| 30 | 80 | 2.55 | 91 | 2.48 |
| 45 | 82 | 2.31 | 93 | 1.43 |
| F2 Value | | | 53 | |

TABLE 2

Provides comparative dissolution profiles of Otezla ®20 mg herein referred as 'reference' versus apremilast tablets 20 mg as per composition of Example 1, herein referred to as 'test' in 0.15% SLS in 25 mM sodium phosphate buffer pH-6.8, RPM-60, Vol-900 ml at 37 ± 0.5° C.

| Time points | Cumulative percent drug release | | | |
|---|---|---|---|---|
| | Reference Product | | Test Product | |
| (minutes) | pH - 6.8 | % RSD | pH - 6.8 | % RSD |
| 10 | 66 | 3.51 | 69 | 3.01 |
| 15 | 70 | 2.81 | 76 | 2.59 |
| 20 | 73 | 2.02 | 81 | 2.40 |
| 30 | 76 | 2.84 | 87 | 1.98 |
| 45 | 79 | 2.32 | 91 | 1.92 |
| F2 Value | | | 53 | |

TABLE 3

Provides comparative dissolution profiles of Otezla ®30 mg herein referred as 'reference' versus apremilast tablets 30 mg as per composition of Example 1, herein referred to as 'test' in 0.15% SLS in 25 mM sodium phosphate buffer pH-6.8, RPM-60, Vol-900 ml at 37 ± 0.5° C.

| Time points | Cumulative percent drug release | | | |
|---|---|---|---|---|
| | Reference Product | | Test Product | |
| (minutes) | pH - 6.8 | % RSD | pH - 6.8 | % RSD |
| 10 | 65 | 1.88 | 68 | 2.85 |
| 15 | 69 | 1.69 | 76 | 2.27 |
| 20 | 73 | 1.60 | 82 | 2.18 |
| 30 | 77 | 1.52 | 88 | 1.33 |
| 45 | 80 | 1.51 | 92 | 0.82 |
| F2 Value | | | 52 | |

Stability Data:

TABLE 4

Provides accelerated stability data of Apremilasttablets10mgas per composition of example 1 packed in PVC/PVDC blister.

| Schedule | Average weight (mg) | Organic Impurities | | | Assay | % Dissolution in 45 mins |
|---|---|---|---|---|---|---|
| | | Desacetyl Impurity | Unknown Impurity | Total Impurity | | |
| Limits | For Record | NMT 0.50% | NMT 0.20% | NMT 1.5% | Between 90.0%-110.0% of label claim | NLT 70% (Q) of the labeled amount is dissolved in 45 minutes. |
| Initial | 103.4 | 0.04 | 0.01 | BRT | 100.8 | 94, 92, 91, 94, 94, 92 Mean: 93 |
| 1 month | 104.8 | 0.05 | 0.00 | 0.05 | 102.7 | 93, 76, 91, 94, 93, 92 Mean: 90 |
| 2 months | 104.6 | 0.05 | 0.01 | 0.05 | 100.1 | 88, 94, 94, 93, 95, 94 Mean: 93 |
| 3 months | 104.4 | 0.02 | 0.01 | BRT | 95.9 | 93, 92, 95, 91, 92, 92 Mean: 93 |
| 6 months | 104.9 | 0.05 | 0.01 | 0.05 | 100.6 | 93, 93, 93, 92, 94, 91 Mean: 93 |

TABLE 5

Provides accelerated stability data of Apremilast tablets 20 mg as per composition of example 1 packed in PVC/PVDC blister.

| Schedule | Average weight (mg) | Organic Impurities | | | Assay | % Dissolution in 45 mins |
| --- | --- | --- | --- | --- | --- | --- |
| | | Desacetyl Impurity | Unknown Impurity | Total Impurity | | |
| Limits | For Record | NMT 0.50% | NMT 0.20% | NMT 1.5% | Between 90.0%-110.0% of label claim | NLT 70% (Q) of the labeled amount is dissolved in 45 minutes. |
| Initial | 204.8 | 0.04 | 0.01 | BRT | 97.7 | 91, 90, 92, 92, 89, 94 Mean: 91 |
| 1 month | 205.9 | 0.05 | BQL | 0.05 | 98.6 | 92, 91, 92, 91, 89, 91 Mean: 91 |
| 2 months | 208.2 | 0.05 | 0.01 | 0.05 | 99.1 | 91, 89, 93, 93, 91, 92 Mean: 92 |
| 3 months | 206.3 | 0.05 | BQL | 0.05 | 95.9 | 91, 90, 92, 91, 91, 91 Mean: 91 |
| 6 months | 206.7 | 0.05 | 0.01 | 0.05 | 98.8 | 92, 91, 94, 95, 94, 94 Mean: 93 |

TABLE 6

Provides accelerated stability data of Apremilast tablets 30 mg as per composition of example 1 packed in PVC/PVDC blister.

| Schedule | Average weight (mg) | Organic Impurities | | | Assay | % Dissolution in 45 mins |
| --- | --- | --- | --- | --- | --- | --- |
| | | Desacetyl Impurity | Unknown Impurity | Total Impurity | | |
| Limits | For Record | NMT 0.50% | NMT 0.20% | NMT 1.5% | Between 90.0%-110.0% of label claim | NLT 70% (Q) of the labeled amount is dissolved in 45 minutes. |
| Initial | 309.2 | 0.04 | 0.01 | BRT | 100.9 | 91, 91, 91, 92, 94, 93 Mean: 92 |
| 1 month | 311.1 | 0.05 | BQL | 0.05 | 101.5 | 92, 93, 93, 92, 91, 91 Mean: 92 |
| 2 months | 312.0 | 0.05 | 0.01 | 0.05 | 101.7 | 89, 89, 89, 91, 90, 88 Mean: 89 |
| 3 months | 312.0 | 0.05 | BQL | 0.05 | 100.1 | 88, 91, 90, 88, 88, 91 Mean: 89 |
| 6 months | 311.9 | 0.05 | 0.01 | 0.05 | 99.5 | 94, 96, 94, 94, 95, 93 Mean: 94 |

We claim:

1. An immediate release stable pharmaceutical composition for oral administration, wherein said composition comprises Apremilast or pharmaceutically acceptable salts thereof, at least one diluent, a binder which is pregelatinized starch and a lubricant;
wherein said pregelatinized starch is present in an amount of about 14% by weight based on the total weight of the composition and said pregelatinized starch is not a disintegrant, and
wherein said composition is a disintegrant free composition.

2. The immediate release stable pharmaceutical composition for oral administration as claimed in claim 1, wherein the composition is in the form of caplets, pills, mini-tablets, granules, pellets, tablets, or capsules.

3. The immediate release stable pharmaceutical composition for oral administration as claimed in claim 1, wherein said composition is in the form of tablets, optionally film coated.

4. The immediate release stable pharmaceutical composition for oral administration as claimed in claim 1, wherein at least one diluent is selected from the group consisting of microcrystalline cellulose, lactose monohydrate, micro fine cellulose, dibasic calcium phosphate, tribasic calcium phosphate, lactose, spray dried lactose, mannitol, maltodextrin, dextrose, magnesium carbonate and a combination thereof.

5. The immediate release stable pharmaceutical composition for oral administration as claimed in claim 1, wherein the lubricant is selected from the group consisting of magnesium stearate, sucrose stearate, calcium stearate, sodium stearyl fumarate and a combination thereof.

6. The immediate release stable pharmaceutical composition as claimed in claim 1, wherein the composition is coated with film coating material selected from polyvinyl alcohol, hydroxy propyl methyl cellulose, carboxymethyl cellulose and any combination thereof.

7. The immediate release stable pharmaceutical composition for oral administration as claimed in claim 1, wherein the composition is prepared by direct compression.

8. The immediate release pharmaceutical composition for oral administration as claimed in claim 1, wherein the composition is stable and shows no change in impurities, dissolution and assay when stored at 40° C.±2° C. &75%±5% relative humidity for a period of at least six months or to the extent necessary for the use of the composition.

9. A process for preparation of disintegrant free immediate release stable pharmaceutical composition comprising Apremilast and one or more pharmaceutical acceptable excipients, wherein said process comprising the steps of:
   a) sifting Apremilast, one or more diluent, and one or more binders through a suitable sieve, wherein one of the one or more binders is pregelatinized starch, wherein said pregelatinized starch is not a disintegrant;
   b) blending mixture of step (a) in a suitable blender;
   c) adding lubricant to blended mixture of step (b) followed by blending to form lubricated blend;
   d) formulating material of step (c) into a suitable dosage form; and
   e) optionally coating the dosage form obtained in step (d), wherein said pregelatinized starch is present in an amount of about 14% by weight based on the total weight of the composition.

* * * * *